United States Patent
Sakamoto et al.

(10) Patent No.: US 12,149,097 B2
(45) Date of Patent: Nov. 19, 2024

(54) WIRELESS POWER RECEPTION CIRCUIT SYSTEM

(71) Applicant: Murata Manufacturing Co., Ltd., Kyoto-fu (JP)

(72) Inventors: Norikazu Sakamoto, Nagaokakyo (JP); Tatsuya Hosotani, Nagaokakyo (JP)

(73) Assignee: Murata Manufacturing Co., Ltd., Kyoto-fu (JP)

( * ) Notice: Subject to any disclaimer, the term of this patent is extended or adjusted under 35 U.S.C. 154(b) by 44 days.

(21) Appl. No.: 18/311,162

(22) Filed: May 2, 2023

(65) Prior Publication Data

US 2023/0275465 A1 Aug. 31, 2023

Related U.S. Application Data

(63) Continuation of application No. PCT/JP2021/040474, filed on Nov. 3, 2021.

(30) Foreign Application Priority Data

Nov. 16, 2020 (JP) ................ 2020-190069

(51) Int. Cl.
*H02J 50/12* (2016.01)
*H02J 7/00* (2006.01)
(Continued)

(52) U.S. Cl.
CPC .......... *H02J 50/12* (2016.02); *H02J 7/00308* (2020.01); *H02J 7/007* (2013.01); *H02M 3/157* (2013.01); *H02J 50/80* (2016.02)

(58) Field of Classification Search
CPC ........ H02J 50/12; H02J 7/00308; H02J 7/007; H02J 50/80; H02J 7/00; H02J 50/10;
(Continued)

(56) References Cited

U.S. PATENT DOCUMENTS

2013/0099588 A1* 4/2013 Yeo .................. H02J 50/10
307/104
2014/0233266 A1* 8/2014 Inukai ............ H02M 3/33507
363/21.01
(Continued)

FOREIGN PATENT DOCUMENTS

JP 2013-191913 A 9/2013
JP 2015-029404 A 2/2015
(Continued)

OTHER PUBLICATIONS

International Search Report issued in PCT/JP2021/040474; mailed Jan. 11, 2022.

*Primary Examiner* — Lincoln D Donovan
*Assistant Examiner* — Alex W Lam
(74) *Attorney, Agent, or Firm* — Studebaker & Brackett PC

(57) ABSTRACT

A wireless power reception circuit system includes a wireless power reception circuit, an electric storage device, a load unit, a digital control circuit, a voltage conversion circuit, a DC-DC converter, smoothing capacitors, a voltage OR circuit, and an external signal setting circuit for resetting the digital control circuit. An enable signal input terminal of the voltage conversion circuit is in a disabled state when the voltage conversion circuit is not controlled by the digital control circuit. The digital control circuit supplies an enable signal to the enable signal input terminal of the voltage conversion circuit when operating the voltage conversion circuit.

20 Claims, 1 Drawing Sheet

(51) Int. Cl.
*H02J 50/80* (2016.01)
*H02M 3/157* (2006.01)

(58) Field of Classification Search
CPC .. H02M 3/157; H02M 1/0032; H02M 1/0048; H02M 1/32; H02M 3/00; A61B 5/00
See application file for complete search history.

(56) References Cited

U.S. PATENT DOCUMENTS

2015/0097439 A1\* 4/2015 Kohout .............. H03K 17/0822
307/104
2018/0143223 A1\* 5/2018 Taya ....................... H02J 50/60

FOREIGN PATENT DOCUMENTS

| | | |
|---|---|---|
| JP | 2015-119559 A | 6/2015 |
| JP | 2017-143704 A | 8/2017 |
| JP | 2019-047627 A | 3/2019 |
| JP | 2019-180234 A | 10/2019 |

\* cited by examiner

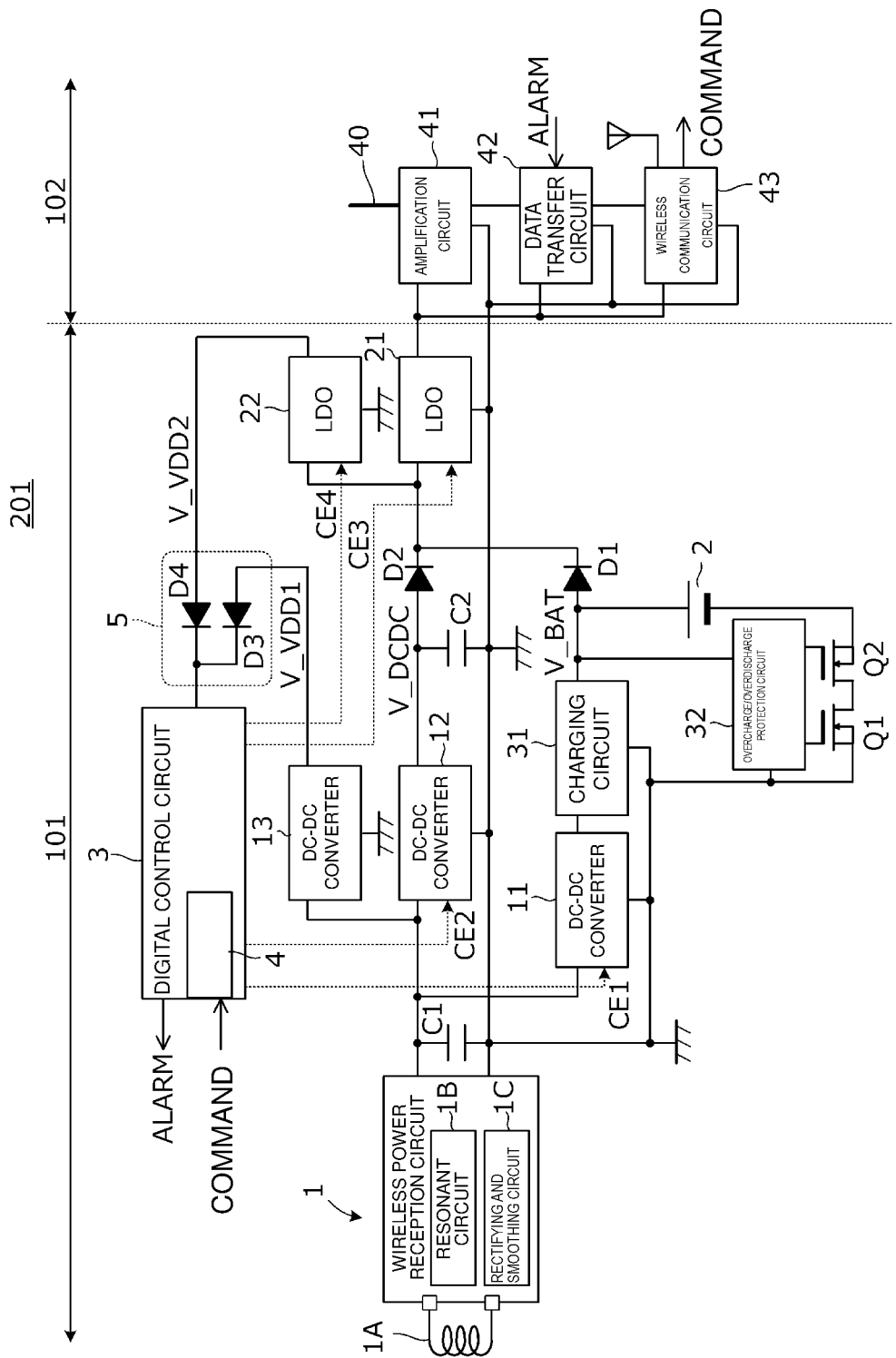

WIRELESS POWER RECEPTION CIRCUIT SYSTEM

CROSS-REFERENCE TO RELATED APPLICATIONS

This application claims benefit of priority to International Patent Application No. PCT/JP2021/040474, filed Nov. 3, 2021, and to Japanese Patent Application No. 2020-190069, filed Nov. 16, 2020, the entire contents of each are incorporated herein by reference.

BACKGROUND

Technical Field

The present disclosure relates to a wireless power reception circuit system that is configured to wirelessly receive power and that includes a digital control circuit configured to manage the supply of power to an internal circuit.

Background Art

For a device for performing a predetermined circuit operation while wirelessly receiving power, together with power reception operation, a power supply management (power management) function of performing, for example, an internal temperature management and a circuit component protection is needed. In particular, safe power management needs to be achieved by, for example, the suppression of heat generation due to a power loss, the protection against an excessive voltage stress or an excessive current stress, and the reset of a digital control circuit that has malfunctioned.

For example, Japanese Unexamined Patent Application Publication No. 2015-29404 describes a wireless power reception device that prevents a circuit element from being broken upon occurrence of an abnormality, such as an overvoltage or an overcurrent, by short-circuiting one of two current routes passing through a rectifier unit when the detection value of a power-reception-side detection unit exceeds a reference value.

Japanese Unexamined Patent Application Publication No. 2015-119559 describes an electronic apparatus that prevents power output from a power supply device from being wasted therein by performing processing for limiting power that a power receiver receives from the power supply device in response to the detection of a predetermined state of the electronic apparatus.

SUMMARY

A digital control circuit for managing the supply of power to an internal circuit needs to continue to stably operate from start to stop to stably perform the above-described power management. A device that wirelessly receives power needs to continue to operate properly until it is safely stopped by using stored power or power from an electric storage device even in the case where it cannot receive power because of, for example, unintended misalignment of a transmission coil with respect to a power reception coil. That is, even if a device that operates a circuit with wirelessly received power undergoes the rapid transition from a state in which wireless power reception is available to a state in which wireless power reception is unavailable, the continuous supply of a voltage to a circuit in the device is needed.

On the other hand, in the case where a digital control circuit malfunctions because of, for example, an unintended error (e.g., freezes because of a latch-up or a hung-up), the digital control circuit needs to be forcedly reset. However, the reset of the digital control circuit is not necessarily easily performed because the amount of power supply voltage for the digital control circuit cannot be rapidly reduced in a circuit configuration for the above-described stable supply of power.

In the case where a circuit for supplying a power supply voltage to the digital control circuit is controlled by the digital control circuit, the circuit for supplying a power supply voltage to the digital control circuit continues to stop when the digital control circuit is powered off and there is no means for restarting the digital control circuit. That is, the stable supply of power to the digital control circuit and the reliable restart of the digital control circuit are opposing requests.

Since the digital control circuit cannot be powered off even in a standby state in which the supply of power to a load is not needed and wireless power reception is not performed, the digital control circuit consumes power in an electric storage device in an apparatus as standby power. Accordingly, a possible standby time is limited because of the capacity of an electric storage device and standby power, and the operation time of a functional circuit operated by a wireless power reception circuit system is shortened.

Therefore, the present disclosure provides a wireless power reception circuit system capable of, even when an apparatus including the wireless power reception circuit system undergoes the rapid transition from a state in which wireless power reception is available to a state in which wireless power reception is unavailable, achieving the continuous supply of a voltage and power to a circuit in the apparatus and also achieving the reduction in standby power and the reliable restart of a digital control circuit.

A wireless power reception circuit system that is an example of the present disclosure includes a wireless power reception circuit, an electric storage device, and a load circuit configured to consume power received by the wireless power reception circuit or power in the electric storage device. Also, the wireless power reception circuit system includes a digital control circuit configured to consume power received by the wireless power reception circuit or power in the electric storage device and to perform control processing to supply or stop supplying power received by the wireless power reception circuit and power in the electric storage device to the load circuit. In addition, the wireless power reception circuit system includes an electric storage device voltage conversion circuit configured to convert a voltage of the electric storage device into a predetermined power supply voltage, a reception voltage conversion circuit configured to convert a voltage received by the wireless power reception circuit into a predetermined power supply voltage, and a smoothing capacitor configured to smooth a power supply voltage for the digital control circuit. Furthermore, the wireless power reception circuit system includes a voltage OR circuit configured to, when an output voltage of the reception voltage conversion circuit is higher than an output voltage of the electric storage device voltage conversion circuit, supply the output voltage of the reception voltage conversion circuit as power for the digital control circuit and configured to, when an output voltage of the reception voltage conversion circuit is lower than an output voltage of the electric storage device voltage conversion circuit, supply an output voltage of the electric storage device as power for the digital control circuit, and an external signal setting circuit configured to reset the digital control circuit in response to an external signal. An enable signal input terminal of the electric storage device voltage conversion circuit is in a disabled state when the electric storage device voltage conversion circuit is not controlled by the digital control circuit. The digital control circuit supplies an enable signal to the enable signal input terminal of the electric storage device voltage conversion circuit when operating the electric storage device voltage conversion circuit.

With the above configuration, the supply of power from the electric storage device to the digital control circuit is seamlessly performed even when the wireless reception of power cannot be performed. Accordingly, a power supply management (power management) function can be performed for circuits in an apparatus, and the continuous supply of a voltage or power to these circuits can be achieved. Even if the digital control circuit freezes because of, for example, an unexpected error, the digital control circuit can be reset by use of an external signal. By providing means for restarting the digital control circuit on the basis of the output voltage of the reception voltage conversion circuit, the digital control circuit can be easily shut down. As a result, the power consumption of the electric storage device can be zero, and standby power can be reduced.

According to the present disclosure, there can be provided a wireless power reception circuit system with which, even when an apparatus including the wireless power reception circuit system undergoes the rapid transition from a state in which wireless power reception is available to a state in which wireless power reception is unavailable, the supply of power from an electric storage device to a digital control circuit can be seamlessly performed, a power supply management (power management) function can be performed for circuits in the apparatus, the continuous supply of a voltage or power to these circuits can be achieved, the reliable restart of the digital control circuit can be achieved, the power consumption of the electric storage device can be zero, and standby power can be reduced.

BRIEF DESCRIPTION OF THE DRAWING

The FIGURE is a block diagram illustrating the configuration of a wireless power reception circuit system 201 according to an embodiment of the present disclosure.

DETAILED DESCRIPTION

The FIGURE is a block diagram illustrating the configuration of a wireless power reception circuit system 201 according to an embodiment of the present disclosure. In this example, the wireless power reception circuit system 201 is an in-vivo implantable small medical device that is used by being embedded (implanted) in the body of, for example, a living person or animal, and wirelessly receives power from the outside of the living body.

The wireless power reception circuit system 201 includes a power reception unit 101 and a load unit 102. The power reception unit 101 includes a wireless power reception circuit 1 and an electric storage device 2. The load unit 102 includes a sensor electrode 40, an amplification circuit 41 for amplifying the detection signal of the sensor electrode 40, a data transfer circuit 42, and a wireless communication circuit 43. The load unit 102 including these circuits is an example of a "load circuit" according to the present disclosure. The amplification circuit 41, the data transfer circuit 42, and the wireless communication circuit 43 operate in response to the supply of a power supply voltage from the power reception unit 101. The sensor electrode 40 and the amplification circuit 41 correspond to a "sensing circuit" according to the present disclosure, and the data transfer circuit 42 and the wireless communication circuit 43 correspond to a "communication circuit" according to the present disclosure.

The wireless power reception circuit 1 includes a power reception coil 1A that is electromagnetically coupled to a power transmission coil (not illustrated), a resonant circuit 1i, and a rectifying and smoothing circuit 1C for rectifying and smoothing the voltage of the resonant circuit.

In the power reception unit 101, a DC-DC converter 11 and a charging circuit 31 are provided between the wireless power reception circuit 1 and the electric storage device 2. The DC-DC converter 11 converts the output voltage of the wireless power reception circuit 1 into a predetermined voltage. The charging circuit 31 charges the electric storage device 2 with power output from the DC-DC converter 11. An overcharge/overdischarge protection circuit 32 is connected to the electric storage device 2. The overcharge/overdischarge protection circuit 32 performs overcharge/overdischarge protection for the electric storage device 2.

A DC-DC converter 12 and a voltage conversion circuit 21 are provided between the wireless power reception circuit 1 and the load unit 102. The DC-DC converter 12 converts the output voltage of the wireless power reception circuit 1 into a predetermined voltage. The voltage conversion circuit 21 stabilizes the output voltage of the DC-DC converter 12 and outputs the stabilized voltage as a power supply voltage for the load unit 102. The voltage conversion circuit 21 is, for example, an LDO (low dropout) linear regulator including series-connected MOS-FETs and a differential amplifier for controlling the gate-source voltage of each of the MOS-FETs using a differential voltage between the output voltage and a reference voltage.

Smoothing capacitors C1 and C2 are provided between the wireless power reception circuit 1 and the load unit 102. The smoothing capacitor C1 suppresses the change in the input voltage for the DC-DC converter 12 even when the output voltage of the wireless power reception circuit 1 changes. The smoothing capacitor C2 suppresses the change in the input voltage for the voltage conversion circuit 21 even when the output voltage of the DC-DC converter 12 changes.

A diode D1 is inserted between the electric storage device 2 and the voltage conversion circuit 21 in a forward direction. A diode D2 is inserted between the DC-DC converter 12 and the voltage conversion circuit 21 in a forward direction. Power is supplied from the DC-DC converter 12 to the voltage conversion circuit 21 at the time of V_DCDC>V_BAT where V_BAT represents the output voltage of the electric storage device 2 and V_DCDC represents the output voltage of the DC-DC converter 12, and power is supplied from the electric storage device 2 to the voltage conversion circuit 21 at the time of V_DCDC<V_BAT.

The power reception unit 101 includes a digital control circuit 3 for controlling each unit in the power reception unit 101. The digital control circuit 3 is a single microcontroller including an external signal setting circuit 4 to be described below. In addition to the DC-DC converter 12, a DC-DC converter 13 is connected to the output portion of the wireless power reception circuit 1. The DC-DC converter 13 corresponds to a "reception voltage conversion circuit" according to the present disclosure. A voltage conversion circuit 22 is connected to the output portion of the DC-DC converter 12 (the cathode of a diode D2). The voltage conversion circuit 22 corresponds to an "electric storage device voltage conversion circuit" according to the present disclosure. Like the voltage conversion circuit 21, the voltage conversion circuit 22 is, for example, an LDO (low dropout) linear regulator. The DC-DC converter 13 stabilizes an output voltage V_VDD1 of the DC-DC converter 13 at a voltage higher than an output voltage V_VDD2 of the voltage conversion circuit 22.

All of the DC-DC converters 11, 12, and 13 are switching regulators each including an inductor, a capacitor, a switching element, and a circuit for controlling the switching element.

A diode D3 is inserted between the output portion of the DC-DC converter 13 and the power input portion of the digital control circuit 3 in a forward direction. A diode D4 is inserted between the output portion of the voltage conversion circuit 22 and the power input portion of the digital control circuit 3 in a forward direction. The diodes D3 and D4 form a voltage OR circuit 5. The diode D3 corresponds to a "first diode" according to the present disclosure, and the diode D4 corresponds to a "second diode" according to the present disclosure.

A voltage obtained by subtracting the forward voltage drop of the diode D3 from V_VDD1 is supplied as a power supply voltage for the digital control circuit 3 at the time of V_VDD1>V_VDD2 where V_VDD1 represents the output voltage of the DC-DC converter 13 and V_VDD2 represents the output voltage of the voltage conversion circuit 22, and a voltage obtained by subtracting the forward voltage drop of the diode D4 from V_VDD2 is supplied as a power supply voltage for the digital control circuit 3 at the time of V_VDD1<V_VDD2.

Each of the DC-DC converter 11, the DC-DC converter 12, the voltage conversion circuit 21, and the voltage conversion circuit 22 has an enable signal input terminal. Each enable signal input terminal is pulled down to a low level (L) by a resistor and operates in response to the input of a chip enable signal of a high level (H) from the digital control circuit 3. The digital control circuit 3 supplies a chip enable signal CE1 to the DC-DC converter 11 and supplies a chip enable signal CE2 to the DC-DC converter 12. The digital control circuit 3 supplies a chip enable signal CE3 to the voltage conversion circuit 21 and supplies a chip enable signal CE4 to the voltage conversion circuit 22.

When the digital control circuit 3 is not activated, the DC-DC converter 11, the DC-DC converter 12, the voltage conversion circuit 21, and the voltage conversion circuit 22 remain at rest because the respective chip enable signals for them are at the low level (L).

When the digital control circuit 3 is activated in response to the wireless reception of power, the digital control circuit 3 sets the respective chip enable signals such that CE1: L, CE2: H, and CE3: H are satisfied, and starts the supply of power to the load unit 102. When the charging of the electric storage device 2 is needed, the digital control circuit 3 sets the respective chip enable signals such that CE1: H, CE2: H, and CE3: H are satisfied and transmits them to charge the electric storage device and supply power to the load unit 102.

Details of the operation of the wireless power reception circuit system 201 described above are as follows.

[Activation in Response to Wireless Reception of Power]

When the wireless power reception circuit 1 wirelessly receives power, a power supply voltage is supplied to the digital control circuit 3 by the route of the wireless power reception circuit 1→the DC-DC converter 13→the diode D3→the digital control circuit 3. The digital control circuit 3 starts to operate and sets the chip enable signal CE4 for the voltage conversion circuit 22 to the high level. As a result, the operation of the voltage conversion circuit 22 is enabled. The output voltage V_VDD1 of the DC-DC converter 13 in a normal state is set to be higher than the output voltage V_VDD2 of the voltage conversion circuit 22. Accordingly, almost no loss is generated in the voltage conversion circuit 22.

Since the enable signal input terminal of the voltage conversion circuit 22 remains at the low level until the digital control circuit 3 is activated, the electric storage device 2 consumes almost no power.

[Operation with Output Power of Wireless Power Reception Circuit 1]

Since the relationship of V_VDD1>V_VDD2 is made in the normal state as described above, a power supply voltage is supplied to the digital control circuit 3 by the route of the wireless power reception circuit 1→the DC-DC converter 13→the diode D3.

The output voltage V_DCDC of the DC-DC converter 12 is higher than the voltage V_BAT of the electric storage device 2 in the normal state (V_DCDC>V_BAT). Accordingly, power is supplied to the load unit 102 by the route of the wireless power reception circuit 1→the DC-DC converter 12→the voltage conversion circuit 21→the load unit 102. The electric storage device 2 is charged by the route of the wireless power reception circuit 1→the DC-DC converter 11→the charging circuit 31→the electric storage device 2.

When the output voltage of the charging circuit 31 is higher than a specified voltage, the overcharge/overdischarge protection circuit 32 turns off switching elements Q1 and Q2 to limit a charge/discharge voltage for the electric storage device 2.

[Operation with Output Power of Electric Storage Device 2]

When the misalignment of a transmission coil with respect to the power reception coil 1A occurs, power received by the wireless power reception circuit 1 decreases. When the voltage V_BAT of the electric storage device 2 is higher than the output voltage V_DCDC of the DC-DC converter 12 (V_DCDC<V_BAT) as a result of the decrease in received power, power is supplied to the load unit 102 by the route of the electric storage device 2→the diode D1→the voltage conversion circuit 21→the load unit 102. A power supply voltage is supplied to the digital control circuit 3 by the route of the electric storage device 2→the diode D1→the voltage conversion circuit 22→the diode D4→the digital control circuit 3.

[Misalignment of Transmission Coil]

When the misalignment of a transmission coil with respect to the power reception coil 1A occurs, power received by the wireless power reception circuit 1 decreases and the digital control circuit 3 outputs an ALARM signal indicating that the received power has decreased to the data transfer circuit 42. The wireless communication circuit 43 wirelessly transmits to the outside a notification that the normal reception of power is unavailable. A user of the wireless power reception circuit system 201 can know the misalignment of the power reception coil 1A with respect to the transmission coil and correct the misalignment.

[Reset of Digital Control Circuit]

When the digital control circuit 3 freezes and does not normally operate for some reason, a reset command signal is externally given to the digital control circuit 3. Upon receiving a reset command, the external signal setting circuit 4 resets the digital control circuit 3. As a result, the freeze state of the digital control circuit 3 is resolved. The above reset command is transmitted from a wireless module that communicates with the wireless communication circuit 43 via the wireless communication circuit 43.

Even if the configuration in which the state of an enable signal input terminal of a circuit for supplying a power supply voltage to the digital control circuit 3 is controlled with a chip enable signal from the digital control circuit 3 is employed and the reset of the digital control circuit 3 is tried by setting the chip enable signal to the low level to interrupt the supply of a power supply voltage to the digital control circuit 3, the digital control circuit 3 cannot be restarted because the enable signal for the circuit for supplying a power supply voltage to the digital control circuit 3 remains at the low level and the decrease in the power supply voltage for the digital control circuit 3 is not resolved.

Lastly, the present disclosure is not limited to the above-described embodiment. A modification and a change can be made as appropriate by those skilled in the art. The scope of the present disclosure is not defined by the above-described embodiment but by the appended claims. Furthermore, the scope of the present disclosure is intended to include all possible modifications and changes from the embodiment within the scopes of the claims and the scopes of equivalents.

For example, the voltage conversion circuits 21 and 22 are not limited to LDOs and may be DC-DC converters.

The external signal setting circuit 4 and the digital control circuit 3 are formed by a single microcontroller in the above example, but may be formed by separate components.

The voltage conversion circuit 22 is disabled in such a manner that the enable signal input terminal thereof is pulled down by a resistor in the above example. In the case where a voltage conversion circuit is used in which it is disabled when the enable signal input terminal thereof is set to the high level, the voltage conversion circuit may have the configuration in which the enable signal input terminal thereof is pulled up by a resistor and it is enabled when a chip enable signal from the digital control circuit is set to the low level.

The load unit 102 includes the sensor electrode 40 functioning as a sensing circuit, the amplification circuit 41, and the data transfer circuit 42 and the wireless communication circuit 43 functioning as a communication circuit in the above example, but does not necessarily have to have this configuration. For example, the load unit 102 may include an A/D converter in the case where the amplification circuit 41 outputs an analog signal.

What is claimed is:

1. A wireless power reception circuit system comprising:
a wireless power reception circuit;
an electric storage device;
a load circuit configured to consume power received by the wireless power reception circuit or power in the electric storage device;
a digital control circuit configured to consume power received by the wireless power reception circuit or power in the electric storage device and to perform control processing to supply or stop supplying power received by the wireless power reception circuit and power in the electric storage device to the load circuit;
an electric storage device voltage conversion circuit configured to convert a voltage of the electric storage device into a predetermined power supply voltage;
a reception voltage conversion circuit configured to convert a voltage received by the wireless power reception circuit into a predetermined power supply voltage;
a smoothing capacitor configured to smooth a power supply voltage for the digital control circuit;
a voltage OR circuit configured to, when an output voltage of the reception voltage conversion circuit is higher than an output voltage of the electric storage device voltage conversion circuit, supply the output voltage of the reception voltage conversion circuit as power for the digital control circuit and configured to, when an output voltage of the reception voltage conversion circuit is lower than an output voltage of the electric storage device voltage conversion circuit, supply an output voltage of the electric storage device as power for the digital control circuit; and
an external signal setting circuit configured to reset the digital control circuit in response to an external signal, wherein
an enable signal input terminal of the electric storage device voltage conversion circuit is in a disabled state when the electric storage device voltage conversion circuit is not controlled by the digital control circuit, and
the digital control circuit is configured to supply an enable signal to the enable signal input terminal of the electric storage device voltage conversion circuit when operating the electric storage device voltage conversion circuit.

2. The wireless power reception circuit system according to claim 1, wherein
the external signal setting circuit and the digital control circuit are configured by a single microcontroller.

3. The wireless power reception circuit system according to claim 1, wherein
the reception voltage conversion circuit is configured to stabilize an output voltage of the reception voltage conversion circuit at a voltage higher than an output voltage of the electric storage device voltage conversion circuit.

4. The wireless power reception circuit system according to claim 1, wherein
the voltage OR circuit includes a first diode connected in series to a route which is configured to supply a reception voltage obtained by rectifying and smoothing power received by the wireless power reception circuit to the digital control circuit and a second diode connected in series to a route which is configured to supply an output voltage of the electric storage device voltage conversion circuit to the digital control circuit.

5. The wireless power reception circuit system according to claim 1, wherein
the reception voltage conversion circuit is configured by a DC-DC converter.

6. The wireless power reception circuit system according to claim 1, wherein
the enable signal input terminal of the electric storage device voltage conversion circuit is brought into the disabled state by being pulled down or pulled up by a resistor.

7. The wireless power reception circuit system according to claim 1, wherein
the load circuit includes a sensing circuit and a communication circuit.

8. The wireless power reception circuit system according to claim 2, wherein the reception voltage conversion circuit is configured to stabilize an output voltage of the reception voltage conversion circuit at a voltage higher than an output voltage of the electric storage device voltage conversion circuit.

9. The wireless power reception circuit system according to claim 2, wherein
the voltage OR circuit includes a first diode connected in series to a route which is configured to supply a reception voltage obtained by rectifying and smoothing power received by the wireless power reception circuit to the digital control circuit and a second diode connected in series to a route which is configured to supply an output voltage of the electric storage device voltage conversion circuit to the digital control circuit.

10. The wireless power reception circuit system according to claim 3, wherein
the voltage OR circuit includes a first diode connected in series to a route which is configured to supply a reception voltage obtained by rectifying and smoothing power received by the wireless power reception circuit to the digital control circuit and a second diode connected in series to a route which is configured to supply an output voltage of the electric storage device voltage conversion circuit to the digital control circuit.

11. The wireless power reception circuit system according to claim 2, wherein
the reception voltage conversion circuit is configured by a DC-DC converter.

12. The wireless power reception circuit system according to claim 3, wherein
the reception voltage conversion circuit is configured by a DC-DC converter.

13. The wireless power reception circuit system according to claim 4, wherein
the reception voltage conversion circuit is configured by a DC-DC converter.

14. The wireless power reception circuit system according to claim 2, wherein
the enable signal input terminal of the electric storage device voltage conversion circuit is brought into the disabled state by being pulled down or pulled up by a resistor.

15. The wireless power reception circuit system according to claim 3, wherein
the enable signal input terminal of the electric storage device voltage conversion circuit is brought into the disabled state by being pulled down or pulled up by a resistor.

16. The wireless power reception circuit system according to claim 4, wherein
the enable signal input terminal of the electric storage device voltage conversion circuit is brought into the disabled state by being pulled down or pulled up by a resistor.

17. The wireless power reception circuit system according to claim 5, wherein
the enable signal input terminal of the electric storage device voltage conversion circuit is brought into the disabled state by being pulled down or pulled up by a resistor.

18. The wireless power reception circuit system according to claim 2, wherein
the load circuit includes a sensing circuit and a communication circuit.

19. The wireless power reception circuit system according to claim 3, wherein
the load circuit includes a sensing circuit and a communication circuit.

20. The wireless power reception circuit system according to claim 4, wherein
the load circuit includes a sensing circuit and a communication circuit.

* * * * *